US012558446B2

(12) United States Patent
Pregenzer

(10) Patent No.: US 12,558,446 B2
(45) Date of Patent: Feb. 24, 2026

(54) TREATMENT UNIT COMPRISING A SENSING UNIT FOR THE MEASUREMENT OF ANTIMICROBIAL ACTIVES

(71) Applicant: Lukas Pregenzer, Mieming (AT)

(72) Inventor: Lukas Pregenzer, Mieming (AT)

( * ) Notice: Subject to any disclaimer, the term of this patent is extended or adjusted under 35 U.S.C. 154(b) by 580 days.

(21) Appl. No.: 17/991,847

(22) Filed: Nov. 22, 2022

(65) Prior Publication Data

US 2023/0364287 A1     Nov. 16, 2023

(30) Foreign Application Priority Data

Dec. 22, 2021    (AT) .............................. A 51039/2021

(51) Int. Cl.
    *A61L 2/24*        (2006.01)
    *A61L 2/18*        (2006.01)
(52) U.S. Cl.
    CPC .................. *A61L 2/24* (2013.01); *A61L 2/18* (2013.01); *A61L 2300/404* (2013.01)
(58) Field of Classification Search
    CPC ....................................................... A61L 2/24
    See application file for complete search history.

(56) References Cited

U.S. PATENT DOCUMENTS 4,938,262 A * 7/1990 Williams .................. A61L 2/24
                                                          141/330
5,158,454 A    10/1992 Viebahn et al.

5,435,969 A * 7/1995 Hoots .................... G01N 33/18
                                                          422/18
7,056,472 B1    6/2006 Behringer
2004/0154965 A1* 8/2004 Baum ..................... C02F 1/008
                                                          210/85
2021/0009453 A1* 1/2021 Boyle ..................... C02F 1/722

FOREIGN PATENT DOCUMENTS

EP        2070866 A1     6/2009
JP        3186257 A      8/1991
JP        2004506473 A   3/2004
WO        2019161334 A1  8/2019

OTHER PUBLICATIONS

Office Action issued in corresponding Japanese Patent Application 2022-186102 dated Sep. 29, 2023 (with English translation) (10 pages).
Search Report issued in corresponding Austria Patent Application No. A51039/2021 dated Aug. 30, 2022 (4 pages).
O'Donnell et al., "Management of dental unit waterline biofilms in the 21st century," Future Microbiology, 2011, vol. 6. No. 10, pp. 1209-1226.
Guo et al., "Advances on Water Quality Detection by UV-Vis Spectroscopy," Applied Sciences, 2020, vol. 10, 6874, doi:10.3390/app10196874 (18 pages).

* cited by examiner

*Primary Examiner* — Kevin Joyner
(74) *Attorney, Agent, or Firm* — Kilyk & Bowersox, P.L.L.C.

(57) ABSTRACT

The invention relates to a medical treatment unit, in particular a dental treatment unit, comprising a water leading system and a measurement unit for the quantitative measurement of an antimicrobial agent content in water contained in the water leading system.

11 Claims, 6 Drawing Sheets

Figure 1:
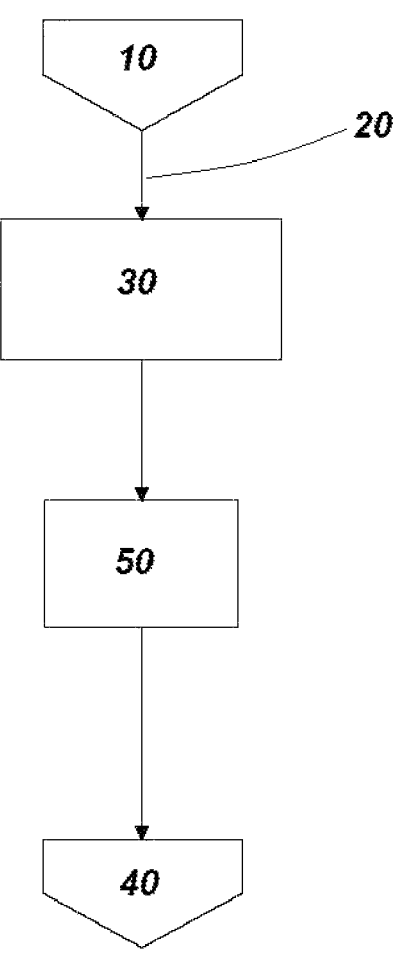

Extinktion 216 nm $y = 52{,}033x + 0{,}0152$
$R^2 = 0{,}9996$

%2-Phenoxyethanol

TREATMENT UNIT COMPRISING A SENSING UNIT FOR THE MEASUREMENT OF ANTIMICROBIAL ACTIVES

This application claims priority to Austrian Patent Application No. A51039/2021, filed Dec. 22, 2021, incorporated in its entirety by reference herein.

The invention relates to a medical treatment unit, in particular a dental treatment unit, comprising a water leading system and a sensing unit for the quantitative measurement of a content of antimicrobial agents in water flowing through the water leading system.

Presently, water treatment equipment is installed ahead of or in medical and, in particular, dental treatment units to treat drinking tap water for use in such treatment units. The equipment uses standard procedures to reduce antimicrobial contamination of the water. Standard procedures comprise, for example, the addition of antimicrobial agents like hydrogen peroxide, silver salts like silver nitrate, phenoxyethanol, hypochloric acid or a hypochlorite, gassing with for example ozone or chlorine gas, or electrolytical cleavage of tap water substances like sodium chloride for the in situ generation of hypochloric acid or a hypochlorite. These procedures to expose water to an antimicrobial agent are designed to assume an exact dosing of the microbial agent to the water. To confirm that the assumed dose of the antimicrobial agent in the water is accurate, treatment unit manufacturers typically recommend weekly probing of the water using, for example, test stripes (applicable to, for example, hydrogen peroxide, chlorine, hypochloric acid or hypochlorites). Further monitoring routines include periodic germ testing through certified laboratories.

These testing methods are snapshots, however, and are prone to error when carried out by a user of the treatment units, during sampling and measurement alike. Hence, they cannot strictly be considered continuous and reliable monitoring methods. Also, they are unsuitable as a data basis for any continuous adaption of the amount of added antimicrobial agent.

The invention aims to provide a solution to the problems rendered above and to provide a treatment unit that improves safety for the patient and legal certainty for the operator when it comes to antimicrobial contamination of treatment water.

Against this background, the invention relates to a medical, in particular dental treatment unit, comprising: a water leading system; a control unit; and a water treatment unit for the addition of an antimicrobial agent to treatment water contained in the water leading system. According to the invention, the medical treatment unit further comprises and a sensing unit for the quantitative measurement of a content of antimicrobial agents in water contained in and preferably flowing through the water leading system, the sensing unit being arranged downstream the water treatment unit in the water leading system.

The control unit is signal linked to the water treatment unit.

The sensing unit is configured to carry out a continuous or at least frequent quantitative measurement of a concentration of an antimicrobial agent added to the water by the water treatment unit. Such control can fulfil all requirements that need to be met in the interest of patient safety, foremost, but also under legal aspects, for example to relieve a doctor or dentist in the case of events that are connected to tap water quality, like cases of legionella contamination, and not in the doctor's or dentist's responsibility.

Suitable antimicrobial agents include hydrogen peroxide, a silver salt like silver nitrate, phenoxyethanol, chlorine, hypochloric acid, a hypochlorite, a quaternary ammonium compound, ozone, iodine, or a combination thereof. Preferred antimicrobial agents include combinations of hydrogen peroxide with a silver salt, or phenoxyethanol, or both.

The antimicrobial agent(s) can be added in the water treatment unit, for example, by addition of solid or liquid chemicals to the water, by gassing the water with gaseous chemicals, or by in situ generation, for example by electrolytic cleavage of substances contained in the tap water.

The invention also encompasses an indirect measurement of the quantity of an antimicrobial agent, which itself may be difficult to detect. In this regard, a marker substance is added to the water in the water treatment unit. The marker substance, which does not need to have antimicrobial activity itself, is added to the water in an amount proportional to the addition amount of the antimicrobial agent. The measurement unit is configured to measure the amount of the marker substance, to enable determination of a content of the antimicrobial agent in the water by proportionality calculations.

In one embodiment, the measurement unit comprises an UV-vis spectrometer, configured for example for transmission or extinction measurement. Such measurement unit can be provided easily and at low cost and, at suitable choice of the measurement window (wavelength window), enables a quantitative measurement of UV detectable antimicrobial agents (e.g. 2-phenoxyethanol, HOCl, etc.) or coloured marker substances.

In case an UV-vis spectrometer is contained in the measurement unit, the measurement path can be 0.5 mm and 20 mm. Preferred measurement path lengths can be 2 mm to 10 mm. A short measurement path can in some cases positively influence measurement accuracy, for example at low light intensity, but can at times be difficult to realize in treatment unit design.

In one embodiment, the measurement unit comprises an (N)IR spectrometer. Such measurement can determine antimicrobial agents like, for example, hydrogen peroxide.

In one embodiment, the measurement unit comprises an electrochemical sensor. Such sensors are suitable for the determination of, for example, ozone.

The measurement unit can also comprise combinations of the above described sensors.

An IR spectrometer quantitative measurement result, for example, varies with water temperature, as intensity peaks, which form a basis for quantitative determination, are influenced by water temperature. Hence, the measurement unit can also comprise a temperature sensor for sensing the water temperature and/or a heating or cooling unit for influencing the water temperature. An electrochemical quantitative measurement result, for example, may vary with the pH value of the water. Hence, the measurement unit may comprise a pH sensor.

In one embodiment, the treatment unit comprises a detecting unit which is signal connected to the control unit. The detecting unit is configured to read in codes, like RFID codes or QR codes, which can be included on antimicrobial agent or marker substance containers to identify the content.

The treatment unit can further comprise an interface, suitable for wire-bound or wireless communication, which is signal connected to the control unit or to the measurement unit. Such interface enables sending measurement signals or values via, e.g., CAN or I2C, an unidirectional or bidirectional data transmission over a network via, e.g., WiFi or BT, and/or communicating with an RFID or QR detecting unit, e.g. for the identification of used antimicrobial agents or marker substances via code reading of containers comprising them.

The control unit can be configured to identify antimicrobial agents or marker substances and concentrations on the basis of a code, which can automatically be recognized by the detecting unit. Required information for such identification can be obtained via the interface over, for example, the internet. In the following, such control unit can, for example, initiate an automatic calibration of sensors or an automatic evaluation of measurement signals.

In one embodiment, the control unit is configured to automatically change the addition amount of the antimicrobial agent in the water treatment unit on the basis of measurement results of the measurement unit. This kind of feedback control allows for optimizing the antimicrobial agent concentration in the water, and hence for optimizing patient safety and antimicrobial agent consumption.

In one embodiment, the treatment unit comprises two serially arranged measurement units. This enables detecting a possible decrease of antimicrobial agent concentration in a section of the water leading system, and hence the possible presence of germs "consuming" the antimicrobial agent in that section. For example, if a concentration decrease in hydrogen peroxide is detected, this is an indicator that an oxidation reaction of organic substances (biofilm, bacteria) is taking place between the measurement points. The concentration difference between the two measurement points can be used to quantify the degree of germ contamination.

The arrangement of the measurement units for such a two point measurement can be such, for example, that a first measurement unit is arranged directly downstream the water treatment unit and a second measurement unit is either arranged close to the exit of the water leading system, which in the case of a dental treatment unit may be close to a handheld dentistry tool, or downstream a section of the water leading system, which is exposed to heat emitted by other components of the treatment unit (e.g. power electronics, servo motors, etc.) and thus potentially more prone to germ growth.

In one embodiment, the measurement result can be used as an input value for a prognosis of temperature dependent germ growth conditions in the treatment unit. In both a one point measurement and a two point measurement, combined evaluation of the measurement values with measurement values of an additional temperature sensor, arranged at the measurement unit or elsewhere in the water leading system, can be used to assess whether certain temperatures promote germ growth. Such information can then be used to adjust addition amounts of the antimicrobial agent to ambient conditions, for example, to increase addition amounts with increasing water temperature.

Each measurement unit can be arranged at a main line or a bypass line of the water leading system. When arranged at a bypass line, switch valves can be used to control a batch operation with periodic measurements. When arranged at the main line, periodic or continuous measurement can be made inline.

The measurement unit can form a separate unit within the treatment unit, or can be included in the water treatment unit.

The invention further relates to a method of measuring a content of an antimicrobial agent in treatment water of a medical, preferably dental treatment unit, wherein the treatment unit comprises a water leading system and a water treatment unit for adding the antimicrobial agent to the treatment water, which is contained in the water leading system, and wherein the content of the antimicrobial agent is measured in a measurement unit arranged downstream the water treatment unit.

Different embodiments of the treatment unit, the antimicrobial agent, the measurement unit, etc. have been described during the above discussion of the treatment unit according to the invention.

Alternative to a configuration, where the measurement unit forms part of the inventive treatment unit, the method of the invention can also be carried out using a measurement unit, which is a separate entity independent of the treatment unit, for example a handheld device or a benchtop device.

Figure 2:
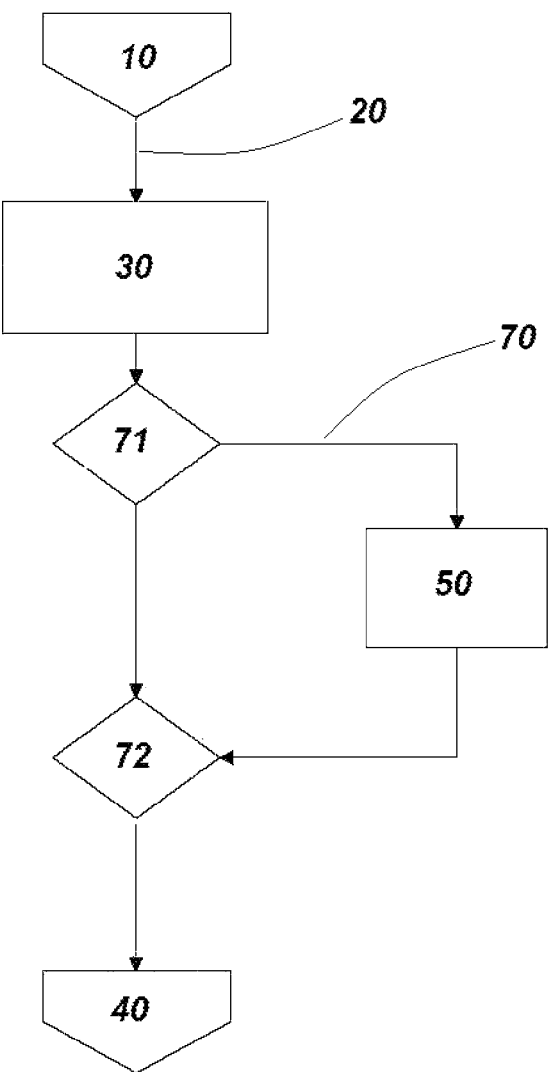
Figure 3:
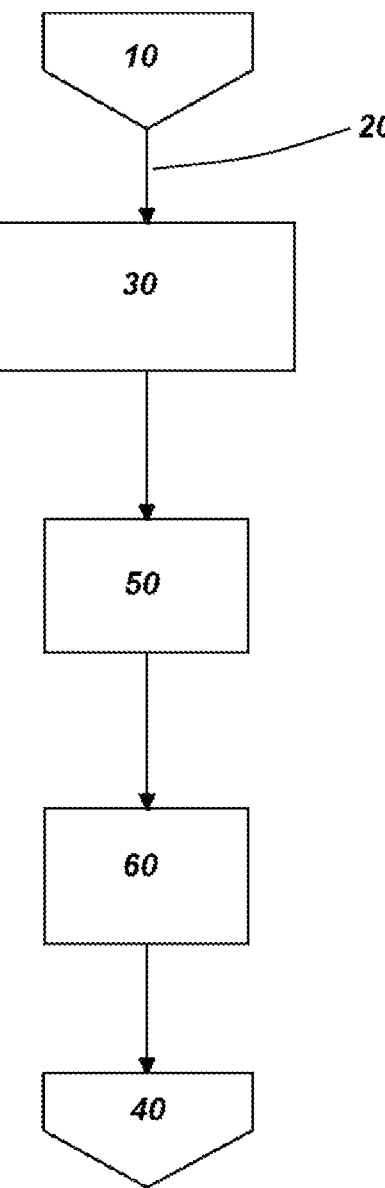
Figure 4:
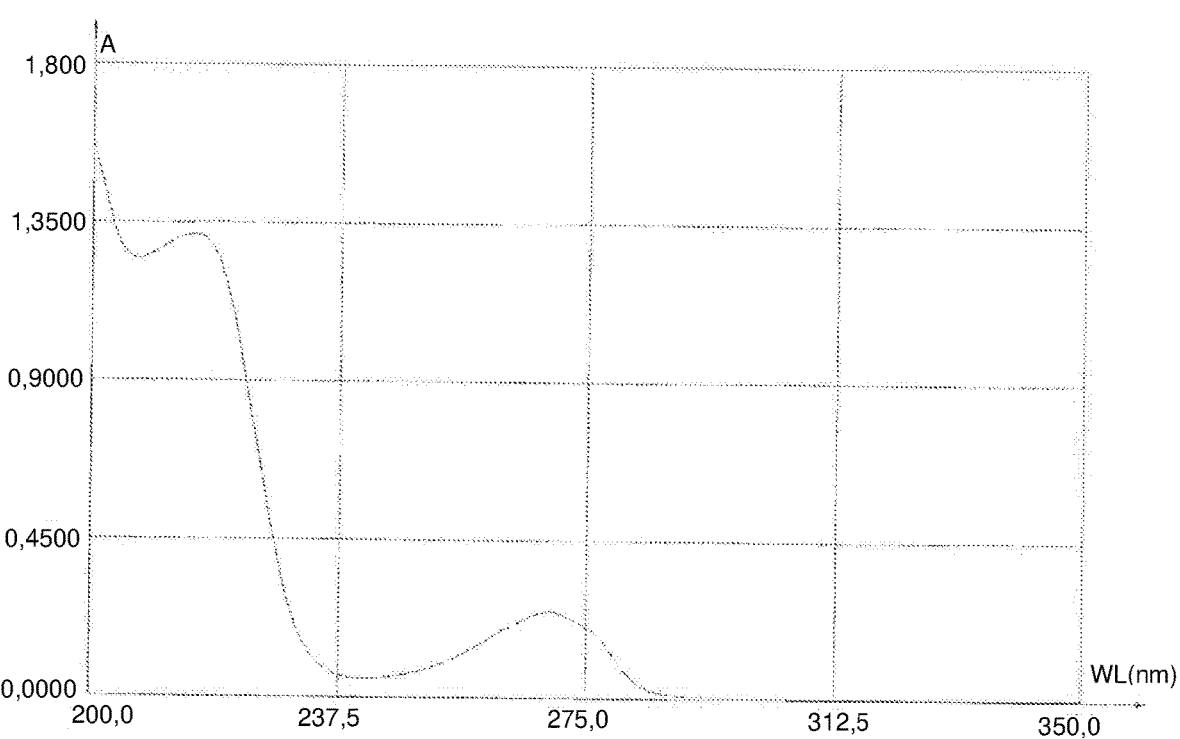
Figure 5:
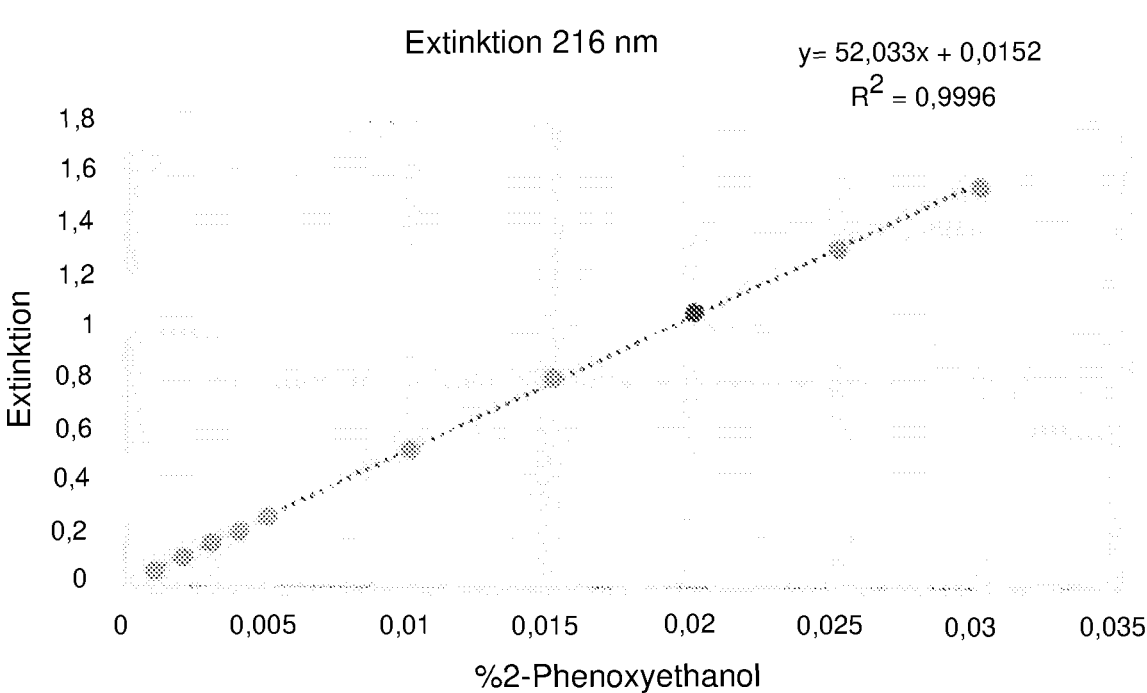
Figure 6:
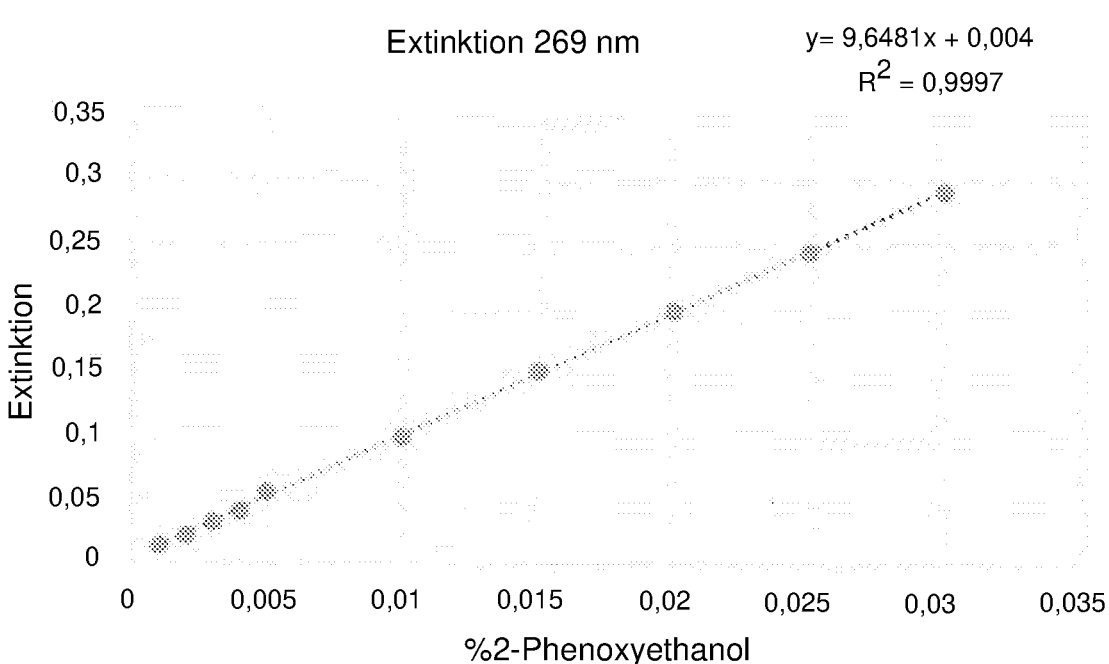

Further details and advantages of the invention become apparent from the following description of specific working examples, with reference to the figures. The figures show:

FIG. 1: a water leading system of a treatment unit according to a first embodiment of the invention;

FIG. 2: a water leading system of a treatment unit according to a second embodiment of the invention;

FIG. 3: a water leading system of a treatment unit according to a third embodiment of the invention;

FIG. 4 a spectrum of an UV extinction measurement of 2-phenoxyethanol;

FIG. 5: a linear fitting of a series of measurements of a an UV extinction measurement of 2-phenoxyethanol at a wavelength of 216 nm; and FIG. 6: a linear fitting of a series of measurements of a an UV extinction measurement of 2-phenoxyethanol at a wavelength of 269 nm.

FIG. 1 shows a schematic illustration of a water leading system of a treatment unit according to a first embodiment of the invention.

The system comprises a water supply 10 at its upstream end, for example a water tap of a building, a main line 20, a water treatment unit 30 arranged at the main line 20, and a consumer 40, for example in the form of an interface for a handheld dentistry tool, at the downstream end of the water leading system.

A measurement unit 50 is arranged at the main line 20 between the water treatment unit 30 and the consumer 40. The measurement unit 50 is described in more detail below.

FIG. 2 shows a schematic illustration of a water leading system of a treatment unit according to an alternative embodiment of the invention.

In this embodiment, the measurement unit 50 is not arranged at the main line 20, but at a bypass line 70, which runs parallel to the main line 20 between the water treatment unit 30 and the consumer 40. Switch valves 71 and 72 are arranged at the branching points of the bypass line 70 for flow control.

A control unit, which is signal connected to the water treatment unit 30, the measurement unit 50 and, in the case of the embodiment of FIG. 2 also to valves 71 and 72, is now shown in the figures.

In the embodiments of FIGS. 1 and 2, an antimicrobial agent is added to the treatment water flowing through the water leading system in the water treatment unit 30. A preferred option for added antimicrobial agent is a combination of hydrogen peroxide and 2-phenoxyethanol. Together with the antimicrobial agent, an UV active marker substance can be added to the water in an amount that is proportional to the added amount of antimicrobial agent.

The measurement unit 50 comprises a UV-vis sensor in combination with a LED light source. The emission and detection ranges of the light source and the sensor can be adjusted to the absorption profile of 2-phenoxyethanol or the marker substance.

Also in the case of using, for example, HOCl, Cl₂, or ClO₂ as an antimicrobial agent, a UV-vis measurement can be used for direct detection of the antimicrobial agent, without using a marker substance. Suitable emission and detection ranges of the light source and the sensor can thereby range from 200 nm to 380 nm, preferably from 240 nm to 340 nm.

Suitable photo diodes for use in a measurement unit 50 of a treatment unit of the invention comprise, for example, SiC photo diodes, which can emit wavelengths between 220 nm and 360 nm.

Alternatively, the measurement unit 50 may comprise a NIR spectrometer, which is suitable, for example, to determine a concentration of hydrogen peroxide. A suitable measurement window may range from 850 nm to 1800 nm.

The measurement devices described above can be implemented into a treatment unit in a simple and cost efficient way. They enable a close control of an antimicrobial agent content in the treatment water, in the batch mode of FIG. 2 as well as in the inline mode of FIG. 1. Thus, it is possible to monitor whether a sufficient amount of antimicrobial agent has been added in the water treatment unit 30 at any time. This increases patient safety and is also suitable to relieve the doctor or dentist in the case of water contamination from the outside, for example, through legionella.

One embodiment of the invention comprises a two-point measurement. While requiring more hardware, such measurement may provide additional information and provides additional options for an automated adaption of added amounts of antimicrobial agent based on measurement values.

FIG. 3 shows a schematic illustration of an embodiment of the invention, which makes use of this embodiment. Generally, the design of this embodiment is similar to the design of FIG. 1, but a second measurement unit 60 is additionally arranged at the main line 60 between the (first) measurement unit 50 and the consumer 40. A section of the water treatment system between the measurement units 50 and 60 is exposed to waste heat from other components of the treatment unit (e.g. power electronics, servo motors), and germ growth can be enhanced in this section.

The measurement units 50 and 60 are both designed as described above in connection with the measurement unit 50 of FIGS. 1 and 2. Further, both measurement units 50 and 60 are equipped with temperature sensors for measuring the temperature of the treatment water.

The two-point measurement is not only suitable to monitor whether a sufficient amount of antimicrobial agent has been added in the water treatment unit 30 at any time, but further enables measuring changes in antimicrobial agent content between the measurement units 50 and 60. In the case of sensors that allow for measuring a hydrogen peroxide content, for example, a reduction in hydrogen peroxide content that may be due to oxidation of organic compounds can be detected. The concentration difference can be considered a representative value for the degree of contamination.

The control unit can be configured to adjust the amount of antimicrobial agent added to the treatment water in the water treatment unit 30 based on that information.

In one embodiment, the control unit can be configured to evaluate the antimicrobial contents and water temperatures measured at measurement units 50 and 60 such as to provide a prognosis of temperature-dependent germ growth, and adjust the amount of antimicrobial agent added to the treatment water in the water treatment unit 30 based on that information.

6

EXAMPLE 1

A concentration measurement of 2-phenoxyethanol based on UV extinction measurement is described.

The test was carried out using an UV spectrophotometer UV-16000PC. Hellma Analytics QS High Precision Cell 1 mm cuvettes were used. Probes comprised an aqueous antimicrobial agent solution, comprising a combination of hydrogen peroxide and 2-phenoxyethanol, and further comprising substances for inhibiting the formation of limescale.

A dilution series of ten different concentrations between 10 and 300 ppm was prepared from the solution. For these probes, extinction was measured in the spectrometer at a resolution of 1 nm over wavelengths between 200 nm and 500 nm. The 1 mm quartz cuvettes were cleaned with deionised water and isopropanol, and dried, between subsequent tests.

FIG. 4 shows a spectrum of an extinction measurement of a probe comprising 0.025% (250 ppm) of 2-phenoxyethanol. The spectrum shows two characteristic peaks at wavelengths of 216 nm and 269 nm.

The following Table 1 shows the extinctions measured at these wavelengths.

TABLE 1

| Concentration 2-phenoxyethanol [ppm] | Extinction at 216 nm | Extinction at 269 nm |
|---|---|---|
| 10 | 0.0622 | 0.0138 |
| 20 | 0.1138 | 0.0216 |
| 30 | 0.1723 | 0.0323 |
| 40 | 0.2178 | 0.0408 |
| 50 | 0.2741 | 0.0558 |
| 100 | 0.5352 | 0.0990 |
| 150 | 0.9162 | 0.1507 |
| 200 | 1.0707 | 0.1984 |
| 250 | 1.3152 | 0.2447 |
| 300 | 1.5582 | 0.2921 |

FIGS. 5 and 6 how a linear fitting of the two measurement series. The result is a linear relationship with a coefficient of determination ($R^2$ value) of 0.9996 at a wavelength of 216 nm and 0.9997 at a wavelength of 269 nm. To meet quality standards for measurements of the kind, the coefficient of determination should exceed 0.9990. This is the case for both measurement rows.

The invention claimed is:

1. A medical treatment unit, comprising:
a water leading system;
a control unit;
a water treatment unit for the addition of an antimicrobial agent to treatment water contained in the water leading system; and
   two serially arranged measurement units connected to the control unit, wherein
   the two serially arranged measurement units are both for the quantitative measurement of a content of antimicrobial agents in the treatment water contained in the water leading system, the two serially arranged measurement units being arranged downstream the water treatment unit in the water leading system, and
   the control unit is configured to detect, based on data provided by the two serially arranged measurement units, a decrease of antimicrobial agent concentration in a section of the water leading system that lies in between the two serially arranged measurement units.

2. The medical treatment unit according to claim 1, wherein the antimicrobial agent is ozone or an aqueous solution of hydrogen peroxide, a silver salt like silver nitrate, 2-phenoxyethanol, chlorine, hypochloric acid, a hypochlorite, an amine, a quaternary ammonium compound, iodine, or a combination thereof.

3. The medical treatment unit according to claim 2, wherein the antimicrobial agent is hydrogen peroxide, a silver salt, 2-phenoxyethanol, or a combination thereof.

4. The medical treatment unit according to claim 1, wherein a marker substance is added to the treatment water in the water treatment unit, wherein the marker substance, which does not have antimicrobial activity itself, is added to the treatment water in an amount proportional to the addition amount of the antimicrobial agent, wherein the two serially arranged measurement units are configured to measure the amount of the marker substance, and wherein the control unit is configured to determine the content of the antimicrobial agent in the treatment water by proportionality calculations.

5. The medical treatment unit according to claim 1, wherein the two serially arranged measurement units comprise a UV-vis spectrometer configured for transmission or extinction measurement; or a NIR spectrometer.

6. The medical treatment unit according to claim 5, wherein a measurement path is 0.5 mm to 20 mm.

7. The medical treatment unit according to claim 6, wherein the measurement path is 2 mm to 10 mm.

8. The medical treatment unit according to claim 1, wherein the two serially arranged measurement units further comprise one or more of a temperature sensor for sensing the water temperature, a heating or cooling unit for influencing the water temperature, a pH sensor, and an electrochemical sensor.

9. The medical treatment unit according to claim 1, further comprising a detecting unit, wherein control unit is configured for automatic identification and quantification of antimicrobial agents in the treatment water on the basis of data received from the detecting unit.

10. The medical treatment unit according to claim 1, further comprising a detecting unit which is signal connected to the control unit, wherein the detecting unit is configured to read in codes, which are optionally included on antimicrobial agent or marker substance containers, and wherein the control unit is configured to identify antimicrobial agents or marker substances and concentrations on the basis of a read in code and initiate an automatic calibration of sensors or an automatic evaluation of measurement signals based thereon.

11. The medical treatment unit according to claim 1, wherein the medical treatment unit is a dental treatment unit.

* * * * *